United States Patent
Kim et al.

(10) Patent No.: US 12,169,193 B2
(45) Date of Patent: Dec. 17, 2024

(54) SAMPLE-COLLECTING DEVICE CAPABLE OF QUANTITATIVE SAMPLING

(71) Applicant: 1DROP INC., Seongnam-Si (KR)

(72) Inventors: Sang Hoon Kim, Seongnam-Si (KR); Ko Bong Choi, Yongin-si (KR); Joo Won Rhee, Seongnam-Si (KR)

(73) Assignee: 1DROP INC., Seongnam-Si (KR)

( * ) Notice: Subject to any disclaimer, the term of this patent is extended or adjusted under 35 U.S.C. 154(b) by 248 days.

(21) Appl. No.: 17/755,067

(22) PCT Filed: Oct. 14, 2020

(86) PCT No.: PCT/KR2020/014001
§ 371 (c)(1),
(2) Date: Apr. 20, 2022

(87) PCT Pub. No.: WO2021/080237
PCT Pub. Date: Apr. 29, 2021

(65) Prior Publication Data
US 2022/0291189 A1 Sep. 15, 2022

(30) Foreign Application Priority Data

Oct. 25, 2019 (KR) .................. 10-2019-0134004
Mar. 3, 2020 (KR) .................. 10-2020-0026689

(51) Int. Cl.
*G01N 33/48* (2006.01)
*G01N 1/20* (2006.01)
*G01N 1/28* (2006.01)

(52) U.S. Cl.
CPC .............. *G01N 33/48* (2013.01); *G01N 1/20* (2013.01); *G01N 1/28* (2013.01)

(58) Field of Classification Search
CPC ........... G01N 33/48; G01N 1/20; G01N 1/28; G01N 33/54387; G01N 33/52;
(Continued)

(56) References Cited

U.S. PATENT DOCUMENTS

2016/0245793 A1* 8/2016 Samsoondar ....... B01L 3/50273
2017/0248622 A1* 8/2017 Khattak ............. G01N 35/0098

FOREIGN PATENT DOCUMENTS

EP 0993614 A1 4/2000
EP 1038176 A2 9/2000
(Continued)

OTHER PUBLICATIONS

International Search Report Issued in Application No. PCT/KR2020/014001, Issued Jan. 29, 2021, 5 pages.
(Continued)

*Primary Examiner* — Suman K Nath
(74) *Attorney, Agent, or Firm* — Osha Bergman Watanabe & Burton LLP

(57) ABSTRACT

The present specification discloses a sample-collecting device capable of quantitative sampling. The sample-collecting device according to the present specification comprises an upper housing and a lower housing which are coupled to be engaged with each other. A film part and a light diffusion part may be provided between the upper housing and the lower housing. A pillar-shaped sample inlet having a central path may be formed in the upper surface of the upper housing, and a sample stopper may be formed as a step on the lower surface of the upper housing. The step is spaced apart by a predetermined distance from a hole in the central path, which is formed in the lower surface of the upper housing, to form a sample storage space, and the step is in contact with the film part to enable sealing so that a sample that has flowed into the sample storage space does not flow out between the sample stopper and the film part.

1 Claim, 4 Drawing Sheets

(58) Field of Classification Search
CPC ....... B01L 2200/027; B01L 2200/0605; B01L 2300/0825; B01L 3/5023
See application file for complete search history.

(56) References Cited

FOREIGN PATENT DOCUMENTS

| | | | |
|---|---|---|---|
| JP | 07055795 | A | 3/1995 |
| KR | 10-2010-0006404 | A | 1/2010 |
| KR | 10-2011-0115216 | A | 10/2011 |
| KR | 10-2013-0080308 | A | 7/2013 |
| KR | 10-2017-0010361 | A | 1/2017 |
| KR | 10-2017-0133238 | A | 12/2017 |
| WO | 2015/179969 | A1 | 12/2015 |
| WO | 2019135526 | A1 | 7/2019 |

OTHER PUBLICATIONS

Written Opinion Issued in Application No. PCT/KR2020/014001, Issued Jan. 29, 2021, 3 pages.
Extended European Search Report issued in the counterpart European Patent Application No. 20879060.0 mailed Nov. 10, 2023 (8 pages).

* cited by examiner

[Fig. 1]
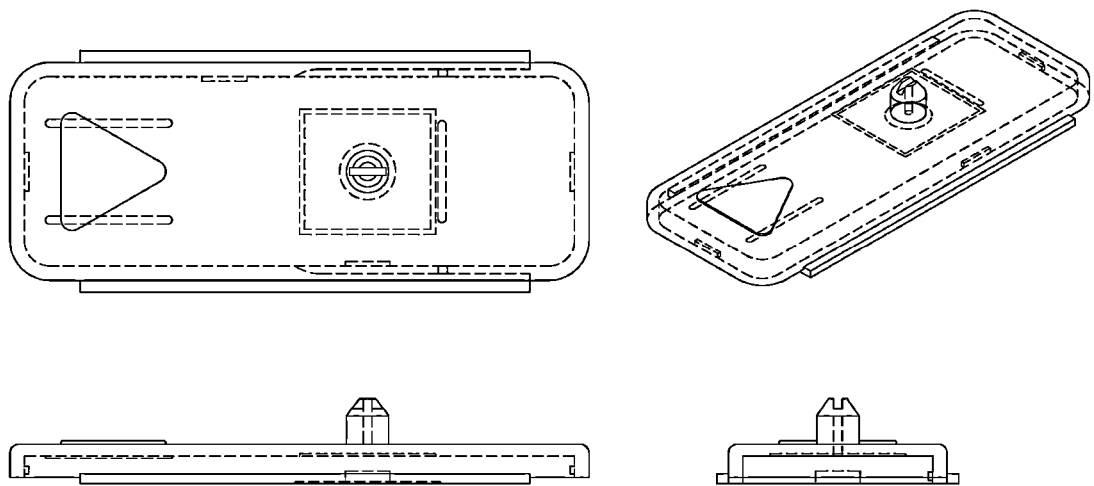
[Fig. 2]
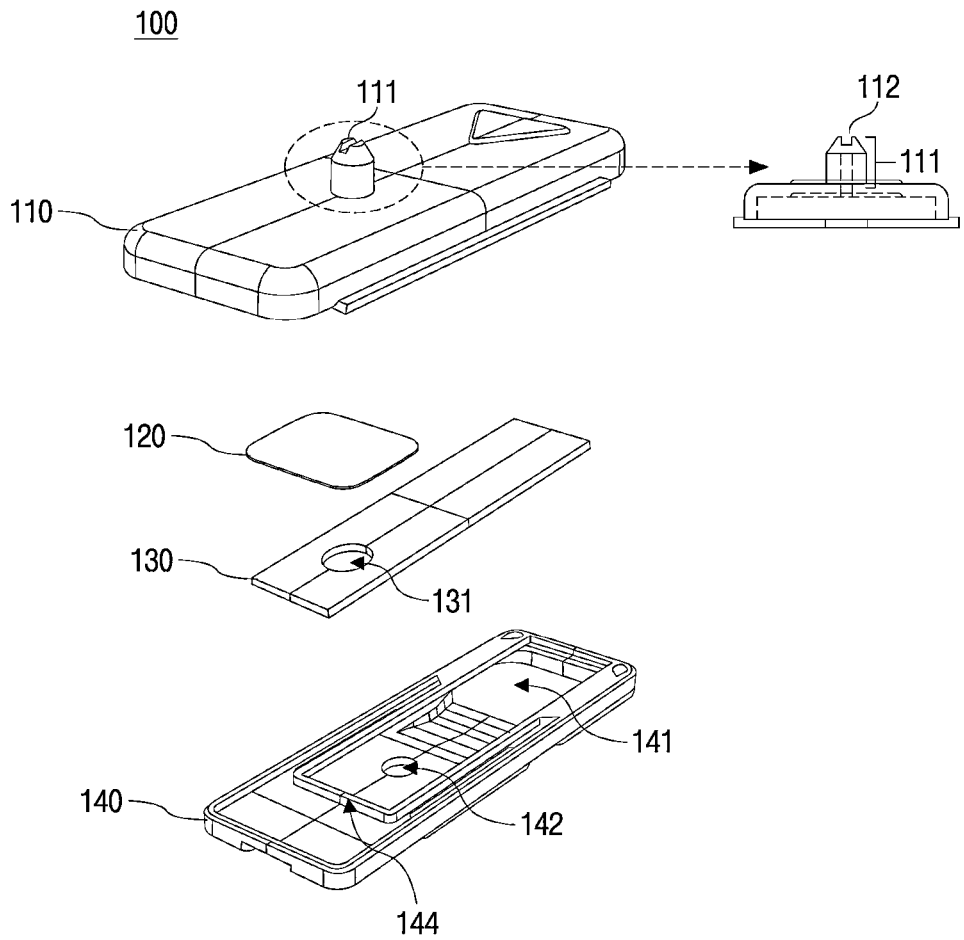

[Fig. 3]
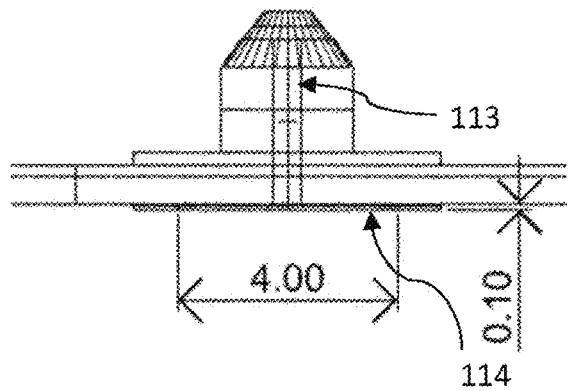
(a)
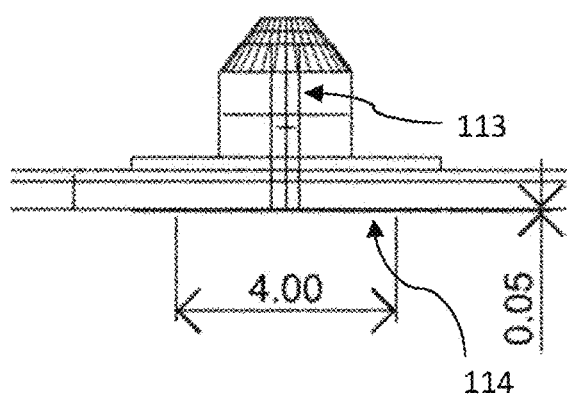
(b)
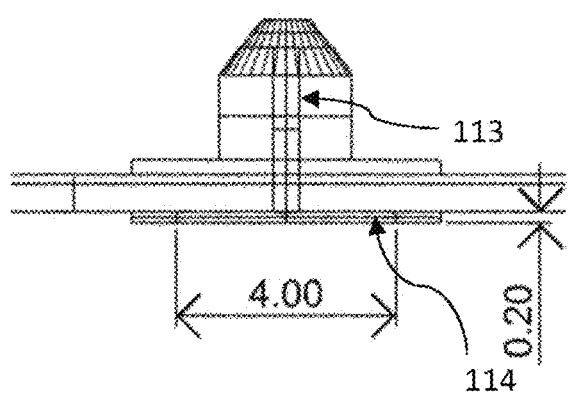
(c)

[Fig. 4]
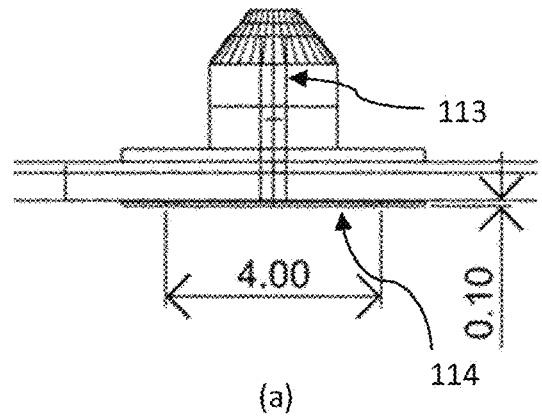
(a)
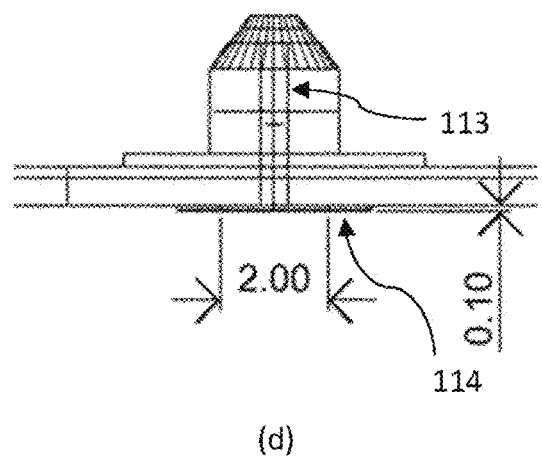
(d)
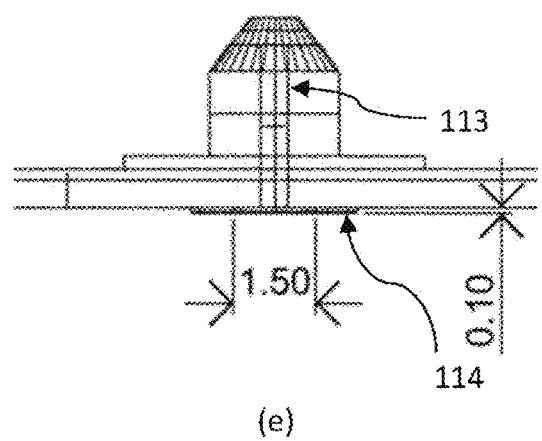
(e)

[Fig. 5]
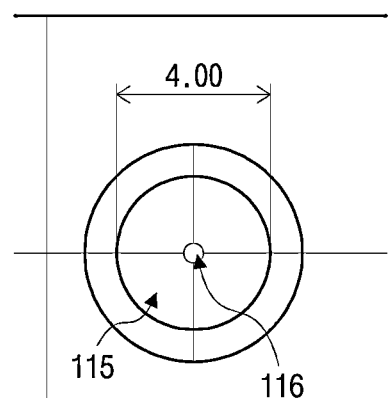
(a)
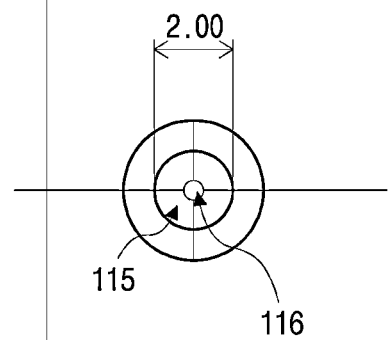
(d)
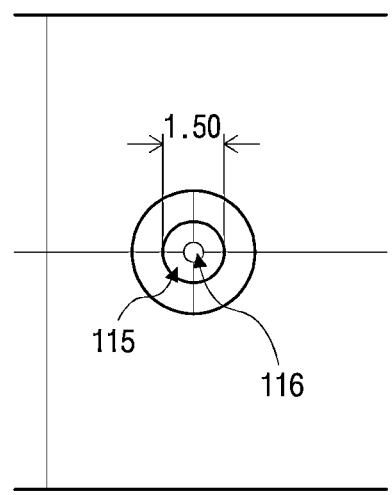
(e)

SAMPLE-COLLECTING DEVICE CAPABLE OF QUANTITATIVE SAMPLING

TECHNICAL FIELD

The present invention relates to a sample-collecting device, and more particularly, to a sample-collecting device capable of quantitative sampling.

This application is accompanied by priority to Korean Patent Application Nos. 10-2019-0134004 and 10-2020-0026689, and all contents described in the specification of the above patent applications can be cited.

BACKGROUND ART

In order to test specific characteristic values using samples such as blood, urine, saliva, and the like, measurement methods using a sample-collecting device, a so-called sensor strip (or biosensor strip), are used. For example, in order to measure blood glucose, a finger is inserted into an inlet of a blood glucose meter and blood is drawn from the fingertip, and when a small amount of blood drawn from the fingertip is placed on a sensor strip inserted into the blood glucose meter, the blood is automatically drawn into an inlet of the sensor strip, and a result value is displayed on a screen of the blood glucose meter.

Such a sensor strip enables the most accurate measurement when a quantitative sample is input. However, in the structure of the sensor strip, in most cases, an excessive amount of sample is input depending on the user, and there are many cases where the deviation of measured values is irregular.

DISCLOSURE

Technical Problem

The present invention is directed to providing a sample-collecting device capable of quantitative sampling.

Objects of the present invention are not limited to the above-described object and other objects that are not described will be clearly understood by those skilled in the art from the following descriptions.

Technical Solution

One aspect of the present invention provides a sample-collecting device including an upper housing having a sample inlet formed in an upper surface thereof and a sample stopper formed on a lower surface thereof, a lower housing having a light entering hole for receiving external light and a photographing hole for photographing the sample input through the sample inlet, a film part which is positioned between the upper housing and the lower housing and on which a sample input through the sample inlet is spread, and a light diffusion part which has a length greater than a distance between the light entering hole and the photographing hole, is positioned between the film part and the lower housing, and has an opening formed at the same position as the photographing hole when positioned between the film part and the lower housing, wherein the sample inlet is formed to have a pillar shape having a central passage, the central passage is connected from an uppermost end (hereinafter referred to as a "contact region") of the sample inlet to the lower surface of the upper housing, and the sample stopper is a step formed on the lower surface of the upper housing, wherein the step is spaced a predetermined distance from a hole of the central passage, which is formed in the lower surface of the upper housing, to form a sample storage space, and the step comes into contact with the film part to seal a gap between the sample stopper and the film part so that the sample input into the sample storage space does not flow out between the sample stopper and the film part.

A side portion of the sample inlet may have a circular pillar shape, and have an upper portion having a truncated cone shape. In this case, a sample input assistance hole having a predetermined width and having a shape which is open from the truncated cone shaped side surface to a contact region may be formed in the upper portion of the sample inlet.

A diameter of the central passage may range from 0.2 mm to 1.5 mm.

A length of the central passage may range from 2.0 mm to 7.0 mm.

A step height of the sample stopper may range from 0.05 mm to 0.20 mm.

The sample stopper may be a step forming a circular sample storage space. In this case, a diameter of the sample storage space may range from 1.0 mm to 4.0 mm.

Preferably, the diameter of the central passage may be 0.7 mm, the length of the central passage may be 3.5 mm, the step height of the sample stopper may be 0.1 mm, and the sample stopper may be a step forming a sample storage space having a diameter of 1.5 mm.

Other specific details of the present invention are included in the detailed description and accompanying drawings.

Advantageous Effects

According to the present invention, a quantitative sample can be sampled regardless of the user's contact time. Since the measurement is made based on the quantitative sample, it is possible to perform more accurate diagnosis.

Effects of the present invention are not limited to the above-described effects and other effects that are not described will be clearly understood by those skilled in the art from the following descriptions.

DESCRIPTION OF DRAWINGS

FIG. 1 illustrates a plan view, a perspective view, a side view, and a front view of a sample-collecting device according to the present invention.

FIG. 2 is an exploded perspective view of the sample-collecting device according to the present invention.

FIGS. 3 and 4 illustrate reference diagrams of a sample inlet.

FIG. 5 illustrates reference diagrams illustrating a portion of a lower surface of an upper housing on which a sample stopper is formed.

MODES OF THE INVENTION

Advantages and features of the present invention and methods of achieving the same will be clearly understood with reference to the accompanying drawings and embodiments described in detail below. However, the present invention is not limited to the embodiments to be disclosed below but may be implemented in various different forms. The embodiments are provided in order to fully describe the present embodiments and fully explain the scope of the present invention to those skilled in the art. The scope of the present invention is only defined by the appended claims.

Terms used in this specification are considered in a descriptive sense only and not for purposes of limitation. In this specification, singular forms include plural forms unless the context clearly indicates otherwise. It will be understood that terms "comprise" and/or "comprising," when used herein, specify some stated components but do not preclude the presence or addition of one or more other components. Like reference numerals indicate like components throughout the specification and the term "and/or" includes each and all combinations of one or more referents. It should be understood that, although the terms "first," "second," etc. may be used herein to describe various components, these components are not limited by these terms. The terms are only used to distinguish one component from another component. Therefore, it should be understood that a first component to be described below may be a second component within the technical scope of the present invention.

Unless otherwise defined, all terms (including technical and scientific terms) used herein can be used as is customary in the art to which the present invention belongs. Also, it will be further understood that terms, such as those defined in commonly used dictionaries, will not be interpreted in an idealized or overly formal sense unless expressly so defined herein.

Spatially-relative terms such as "below," "beneath," "lower," "above," and "upper" may be used herein for ease of description to describe the relationship of one component and other components as illustrated in the drawings. The spatially-relative terms should be understood to include different directions of the component when being used or operating, in addition to the direction illustrated in the drawing. For example, when the component in the drawings is turned over, components described as "below" or "beneath" other components would then be oriented "above" the other components. Therefore, an exemplary term "below" may encompass both an orientation of above and below. Components may be oriented in different directions so that spatially-relative terms may be interpreted according to the arrangement.

Hereinafter, the embodiments of the present invention will be described in detail with reference to the accompanying drawings.

FIG. 1 illustrates a plan view, a perspective view, a side view, and a front view of a sample-collecting device according to the present invention.

FIG. 2 is an exploded perspective view of the sample-collecting device according to the present invention.

Referring to FIG. 1, the sample-collecting device 100 according to the present invention may include an upper housing 110, a film part 120, a light diffusion part 130, and a lower housing 140.

The upper housing 110 may be made of a polymer synthetic material, so-called plastic, and may be manufactured using an injection molding method. A sample inlet 111 is a hole through which a material to be measured, such as blood, urine, saliva, etc. is input, and a user may input a sample into the sample-collecting device 100 through the sample inlet 111 formed in an upper surface of the upper housing 110.

The upper housing 110 and the lower housing 140 may have shapes corresponding to each other. In addition, the lower housing 140 may be coupled to be engaged with the upper housing 110 (e.g., a forced fit method).

A light entering hole 141 for receiving external light and a photographing hole 142 for photographing the input sample may be formed in the lower housing 140. The sample-collecting device 100 according to the present invention may be a device necessary for performing a colorimetric method using a camera included in a mobile communication terminal. In the mobile communication terminal, the camera and a light source that emits light may be configured to be adjacent on the same surface. In this case, the sample-collecting device 100 according to the present invention may be positioned in front of the camera of the mobile communication terminal, and the light source may emit light and then the sample may be photographed so that the colorimetric method may be performed. The light entering hole 141 is a hole through which the light emitted from the light source (e.g., a light-emitting diode (LED)) installed in the mobile communication terminal enters the inside of the sample-collecting device 100. In addition, the photographing hole 142 is a hole through which the camera installed in the mobile communication terminal may photograph the sample.

The sizes and positions of the photographing hole 142 and the light entering hole 141 may vary depending on positions of the light source and the camera installed in the mobile communication terminal to be used. The mobile communication terminal may include a mobile phone, a smartphone, a laptop computer, a digital broadcasting terminal, a personal digital assistant (PDA), a portable multimedia player (PMP), a navigation system, a slate personal computer (PC), a tablet PC, a Ultrabook, a wearable device (e.g., a smartwatch, smart glasses, and a head mounted display (HMD)), or the like. However, the present invention is not limited to a specific mobile communication terminal.

The film part 120 may be positioned between the upper housing 110 and the lower housing 140. The film part 120 is a portion on which a sample solution input through the sample inlet 111 spreads. In particular, when blood is input through a porous structure, the film part 120 may be made of a material capable of separating only a blood plasma component from whole blood. For the material and/or structure of the film part 120, the content filed through Korean Patent Application No. 10-2018-0001815 (title: Strip for measuring biomaterials) will be cited, and detailed descriptions thereof will be omitted.

The light diffusion part 130 may have a length greater than a distance between the light entering hole 141 and the photographing hole 142 and may be positioned between the film part 120 and the lower housing 140. The light diffusion part 130 is a component which light first reaches when the light emitted from the light source installed in the mobile communication terminal is enters the inside of the sample-collecting device 100 through the light entering hole 141. The light is diffused and scattered laterally through the light diffusion part 130 so that the light reaches the film part 120 on which the sample is placed.

Further, when the light diffusion part 130 is positioned between the film part 120 and the lower housing 140, the light diffusion part 130 may have an opening 131 formed at the same position as the photographing hole 142. The camera installed in the mobile communication terminal may photograph the sample on the film part 120 through the opening 131.

Meanwhile, in the lower housing 140, a light diffusion part seating groove 144 in which the light diffusion part 130 may be seated may be formed. A depth of the light diffusion part seating groove 144 may be identical to a height of the light diffusion part 130, and the light diffusion part seating groove 144 may have a size corresponding to a length and width of the light diffusion part 130.

The sample inlet 111 may be formed to have a pillar shape having a central passage.

According to an embodiment of the present invention, a side portion of the sample inlet 111 may have a circular pillar shape, and have an upper portion having a truncated cone shape. Further, referring to an auxiliary image illustrated at the right side of the upper housing 110 in FIG. 2, in the upper portion of the sample inlet 111, a sample input assistance hole 112 having a predetermined width and having a shape which is open from the truncated cone shaped side surface to a contact region may be formed. When the user covers an uppermost end (hereinafter referred to as a "contact region") of the sample inlet 111 with his or her finger for blood sampling, the sample input assistance hole 112 is not directly covered by the finger, but may be covered by the blood on the fingertip. Accordingly, a surface area of a portion in which the blood is brought into contact with the contact region is increased, and thus a large amount of blood may be input into the sample inlet 111. The central passage will be described with reference to FIGS. 3 and 4.

FIGS. 3 and 4 illustrate reference diagrams of the sample inlet.

Referring to FIGS. 3 and 4, a central passage 113 may be connected from the uppermost end (contact region) of the sample inlet 111 to a lower surface of the upper housing 110. Therefore, the sample may be input into the sample-collecting device 100 along the central passage 113 and may reach the film part 120.

A sample stopper 114 may be formed on the lower surface of the upper housing 110.

Referring to FIGS. 3 and 4, it can be seen that the sample inlet 111 is illustrated. The sample stopper 114 may be formed as a step having a predetermined height from the lower surface of the upper housing 110. In this case, a boundary of the sample stopper 114 may be formed in a stepped manner from the lower surface of the upper housing 110 or may be formed in an inclined manner.

FIG. 5 illustrates reference diagrams illustrating a portion of the lower surface of the upper housing 110 on which the sample stopper 114 is formed.

Referring to FIG. 5, it can be seen that a hole 116 of the central passage 113 is formed in the lower surface of the upper housing 110. The hole 116 may be referred to as a "stopper hole."

The step may be spaced a predetermined distance from the stopper hole 116 so that the sample stopper 114 may form a sample storage space 115. In a state in which the upper housing 110 is coupled to the lower housing 140, a surface of the sample stopper 114 comes into contact with the film part 120. In this case, the sample stopper 114 and the film part 120 come into contact with each other to fully seal a gap therebetween, and thus the sample cannot flow out of the sample stopper 114 and remains inside. That is, the sample stopper 114 comes into contact with the film part 120, and thus a gap between sample stopper 114 and the film part 120 may be sealed so that the sample input into the sample storage space 115 does not flow out between the sample stopper 114 and the film part 120. Preferably, the gap between the sample stopper 114 and the film part 120 may be sealed to the degree that not only a fluid but also gas does not pass. Therefore, the sample input through the sample inlet 111 reaches the sample storage space 115 through the stopper hole 116, and when the sample that reaches the sample storage space 115 is no longer spread due to the sample stopper 114, the sample is filled as much as the size of the sample storage space 115.

More sample (blood, urine, etc.) than necessary may be input into the sample-collecting device according to the related art, that is, the sensor strip, by the user. An excessive amount of sample is the cause of lowering the accuracy of diagnosis such as a colorimetric method or the like. Therefore, in order to improve the accuracy of diagnosis such as a colorimetric method or the like, it is necessary to input a sample suitable for an amount of a reaction reagent applied to the film part 120.

An advantage of the sample-collecting device 100 according to the present invention is the achievement of an appropriate input amount of sample. It is assumed that the user inputs his or her blood into the sample-collecting device 100 through finger blood sampling. When the user puts his or her finger on the contact region (blood input operation), the blood passes through the central passage 113, which passes through the sample inlet 111, and reaches the sample storage space 115. In this case, the blood is no longer spread due to the sample stopper 114, and the blood is filled from the sample storage space 115 through the central passage 113 to the contact region. As a result, no more blood is input into the sample inlet 111 (blood input stopping operation). Further, while the user touches the contact region with his or her finger, the blood filling the central passage 113 and the like is blocked from atmospheric pressure, and thus the blood does not go down in a state in which the central passage 113 is filled (input blood stopping operation). Thereafter, when the user separates his or her finger from the contact region, the blood filling the central passage 113 and the like flows downward through the sample inlet 111 due to the atmospheric pressure (blood input completion operation). When the blood input operation, the blood input stopping operation, the input blood stopping operation, and the blood input completion operation are performed, only as much blood as the amount filling the central passage 113 and the sample storage space 115 is input into the sample-collecting device 100. That is, only an amount of blood corresponding to areas of the central passage 113 and the sample storage space 115 is input into the sample-collecting device 100, regardless of the length of time the user's finger touches the contact region.

Therefore, the input amount of sample may be set by the areas of the central passage 113 and the sample storage space 115, but the areas of the central passage 113 and the sample storage space 115 should be determined in consideration of material properties such as density and viscosity of the sample.

According to an embodiment of the present invention, a diameter of the central passage 113 may range from 0.2 mm to 1.5 mm.

According to an embodiment of the present invention, a length of the central passage 113 may range from 2.0 mm to 7.0 mm.

According to an embodiment of the present invention, a step height of the sample stopper 114 may range from 0.05 mm to 0.20 mm.

According to an embodiment of the present invention, the sample stopper 114 may be a step forming a circular sample storage space 115. Further, a diameter of the sample storage space may range from 1.0 mm to 4.0 mm.

Meanwhile, when the sample is blood, the applicant conducted experiments on whether an appropriate amount of blood is input according to a size of each structure.

Referring to FIG. 3 again, it can be seen that the step height of the sample stopper 114 is changed. In Example a of FIG. 3, the step height of the sample stopper 114 is 0.1 mm, in Example b of FIG. 3, the step height of the sample stopper 114 is 0.05 mm, and in Example c of FIG. 3, the step height of the sample stopper 114 is 0.2 mm. Results of experiments in which the blood was input five times for each of Examples a, b, and c are as in Table 1 below.

TABLE 1

| Input weight (mg) | a | b | c |
|---|---|---|---|
| 1$^{st}$ input | 2.9 | 3.3 | 3.5 |
| 2$^{nd}$ input | 3.6 | 3.6 | — |
| 3$^{rd}$ input | 3.5 | 3.6 | 3.0 |
| 4$^{th}$ input | 3.5 | 3.1 | — |
| 5$^{th}$ input | 3.2 | 2.8 | 3.5 |
| AVER | 3.34 | 3.28 | 3.33 |
| SD | 0.29 | 0.34 | 0.29 |
| % CV | 8.68 | 10.43 | 8.66 |

In Table 1 above, the unit of weight of the input blood is milligram (mg), AVER denotes an average weight of the input blood, SD denotes a standard deviation, and CV denotes a coefficient of variation. Further, in the experiments illustrated in FIG. 3, the diameter of the central passage is 0.7 mm, the length of the central passage is 3.5 mm, and the diameter of the sample storage space is 4.0 mm.

Referring to Table 1, a value of the CV is the lowest in Example c. However, there was a case in which no blood was input in the 2$^{nd}$ input and the 4$^{th}$ input. The step height of the sample stopper 114 is related to the pressure applied to the film part 120 in a state in which the upper housing 110 and the lower housing 140 are coupled to each other. When the step height of the sample stopper 114 is too high, the pressure applied to the film part 120 is increased and, accordingly, air that is present in the sample storage space 115 before the blood is input cannot be discharged, and thus it is determined that the blood is not input. Meanwhile, in Example b, the step height of the sample stopper 114 is too low, and thus the input blood passed over the sample stopper 114 and leaked sideways. Therefore, the step height of the sample stopper 114 is preferably 0.1 mm.

Next, referring to FIGS. 4 and 5, it can be seen that the diameter of the sample storage space 115 is changed. In Example a of FIG. 4, the diameter of the sample storage space 115 is 4.0 mm, in Example d of FIG. 4, the diameter of the sample storage space 115 is 2.0 mm, and in Example e of FIG. 4, the diameter of the sample storage space 115 is 1.5 mm. Results of experiments in which the blood was input five times for each of Examples a, d, and e are as in Table 2 below.

TABLE 2

| Input weight (mg) | a | d | e |
|---|---|---|---|
| 1$^{st}$ input | 2.9 | 3.4 | 3.0 |
| 2$^{nd}$ input | 3.6 | 3.0 | 2.8 |
| 3$^{rd}$ input | 3.5 | 3.3 | 3.0 |
| 4$^{th}$ input | 3.5 | 2.8 | 2.7 |
| 5$^{th}$ input | 3.2 | 3.0 | 2.8 |
| AVER | 3.34 | 3.10 | 2.86 |
| SD | 0.29 | 0.24 | 0.13 |
| % CV | 8.68 | 7.90 | 4.69 |

In Table 2 above, the unit of weight of the input blood is mg, AVER denotes an average weight of the input blood, SD denotes a standard deviation, and CV denotes a coefficient of variation. Further, in the experiments illustrated in FIGS. 4 and 5, the diameter of the central passage is 0.7 mm, the length of the central passage is 3.5 mm, and the step height of the sample stopper is 0.1 mm.

Referring to Table 2, a value of the CV is the lowest in Example e. Therefore, the diameter of the sample storage space 115 is preferably 1.5 mm.

While embodiments of the present inventive concept have been described with reference to the accompanying drawings, it will be understood by those skilled in the art that various modifications can be made without departing from the scope of the present inventive concept and without changing essential features. Therefore, the above-described embodiments should be considered in a descriptive sense only and not for purposes of limitation.

REFERENCE NUMERALS

100: SAMPLE-COLLECTING DEVICE
110: UPPER HOUSING
111: SAMPLE INLET
112: SAMPLE INPUT ASSISTANCE HOLE
113: CENTRAL PASSAGE
114: SAMPLE STOPPER
115: SAMPLE STORAGE SPACE
116: STOPPER HOLE
120: FILM PART
130: LIGHT DIFFUSION PART
140: LOWER HOUSING

The invention claimed is:

1. A sample-collecting device comprising:
an upper housing having a sample inlet formed in an upper surface thereof and a sample stopper formed on a lower surface thereof;
a lower housing coupled to the upper housing; and
a film part which is positioned between the upper housing and the lower housing and on which a sample input through the sample inlet is spread,
wherein the sample inlet is formed to have a pillar shape having a central passage,
the central passage is connected at a contact region of the sample inlet from an uppermost end to the lower surface of the upper housing, and
the sample stopper is a step formed on the lower surface of the upper housing, wherein the step is spaced a predetermined distance from a hole of the central passage, which is formed in the lower surface of the upper housing, to form a sample storage space, and the step comes into contact with the film part to seal a gap between the sample stopper and the film part so that the sample input into the sample storage space does not flow out between the sample stopper and the film part, wherein
a diameter of the central passage is 0.7 mm;
a length of the central passage is 3.5 mm;
a step height of the sample stopper is 0.1 mm; and
the sample stopper is a step forming a circular sample storage space having a diameter of 1.5 mm.

* * * * *